US00PP26560P2

(12) United States Plant Patent
Moen

(10) Patent No.: US PP26,560 P2
(45) Date of Patent: Mar. 29, 2016

(54) ***GERBERA* PLANT NAMED 'FLOCANOES'**

(50) Latin Name: *Gerbera hybrida*
Varietal Denomination: Flocanoes

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 150 days.

(21) Appl. No.: 13/999,714

(22) Filed: Mar. 17, 2014

(51) Int. Cl.
*A01H 5/02* (2006.01)

(52) U.S. Cl.
USPC ..... Plt./357

(58) Field of Classification Search
USPC ..... Plt./357
See application file for complete search history.

*Primary Examiner* — Keith Robinson
(74) *Attorney, Agent, or Firm* — C. A. Whealy

(57) ABSTRACT

A new and distinct cultivar of *Gerbera* plant named 'Flocanoes', characterized by its compact, broadly upright and uniformly mounding plant habit; dense and bushy appearance; numerous inflorescences with orange and yellow-colored ray florets; upright and strong scapes; and good garden performance.

1 Drawing Sheet

Botanical designation: *Gerbera hybrida.*
Cultivar denomination: 'FLOCANOES'.

BACKGROUND OF THE INVENTION

The present invention relates to a new and distinct cultivar of *Gerbera* plant, botanically known as *Gerbera hybrida* and hereinafter referred to by the name 'Flocanoes'.

The new *Gerbera* plant is a product of a planned breeding program conducted by the Inventor in De Kwakel, The Netherlands. The objective of the breeding program is to create new compact potted *Gerbera* plants with numerous attractive inflorescences and good garden performance.

The new *Gerbera* plant originated from a cross-pollination made during the spring of 2010 in De Kwakel, The Netherlands of a proprietary selection of *Gerbera hybrida* identified as code number FL 12, not patented, as the female, or seed, parent with a proprietary selection of *Gerbera hybrida* identified as code number FL 63, not patented, as the male, or pollen, parent. The new *Gerbera* plant was discovered and selected by the Inventor as a single flowering plant within the progeny of the stated cross-pollination in a controlled greenhouse environment in De Kwakel, The Netherlands during the summer of 2011.

Asexual reproduction of the new *Gerbera* plant by cuttings and by tissue culture in a controlled environment in De Kwakel, The Netherlands since the summer of 2011 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Flocanoes'.

These characteristics in combination distinguish 'Flocanoes' as a new and distinct *Gerbera* plant:

1. Compact, broadly upright and uniformly mounding plant habit.
2. Dense and bushy appearance.
3. Numerous inflorescences with orange and yellow-colored ray florets.
4. Upright and strong scapes.
5. Good garden performance.

Plants of the new *Gerbera* differ from plants of the female parent selection in the following characteristics:

1. Plants of the new *Gerbera* have larger leaves than plants of the female parent selection.
2. Plants of the new *Gerbera* have larger inflorescences than plants of the female parent selection.
3. Plants of the new *Gerbera* and the female parent selection differ in ray floret coloration.

Plants of the new *Gerbera* differ from plants of the male parent selection in the following characteristics:

1. Plants of the new *Gerbera* have smaller leaves than plants of the male parent selection.
2. Plants of the new *Gerbera* have smaller inflorescences than plants of the male parent selection.
3. Plants of the new *Gerbera* and the male parent selection differ in ray floret coloration.

Plants of the new *Gerbera* can be compared to plants of the *Gerbera hybrida* 'Redwood', disclosed in U.S. Plant Pat. No. 21,755. Plants of the new *Gerbera* differ from plants of 'Redwood' in the following characteristics:

1. Plants of the new *Gerbera* have smaller leaves than plants of 'Redwood'.
2. Plants of the new *Gerbera* have smaller inflorescences than plants of 'Redwood'.
3. Plants of the new *Gerbera* have smaller ray florets than plants of 'Redwood'.
4. Plants of the new *Gerbera* and 'Redwood' differ in ray floret color.

BRIEF DESCRIPTION OF THE PHOTOGRAPHS

The accompanying photographs illustrate the overall appearance of the new *Gerbera* plant showing the colors as true as it is reasonably possible to obtain in colored reproductions of this type. Colors in the photographs may differ slightly from the color values cited in the detailed botanical description which accurately describe the colors of the new *Gerbera* plant.

The main photograph comprises a side perspective view of a typical flowering plant of 'Flocanoes' grown in a container.

The smaller photograph is a close-up view of a typical inflorescence of 'Flocanoes'.

DETAILED BOTANICAL DESCRIPTION

The aforementioned photographs and following observations and measurements describe plants grown during the autumn and winter in 19-cm containers in a glass-covered greenhouse in De Kwakel, The Netherlands and under cultural practices typical of commercial *Gerbera* production. During the production of the plants, day temperatures ranged from 18° C. to 20° C. and night temperatures averaged 18° C. Plants were six months old when the photographs were taken and 30 weeks old when the description was taken. In the following description, color references are made to The Royal Horticultural Society Colour Chart, 2007 Edition, except where general terms of ordinary dictionary significance are used.

Botanical classification: *Gerbera hybrida* 'Flocanoes'.

Parentage:

*Female, or seed, parent.*—Proprietary selection of *Gerbera hybrida* identified as code number FL 12, not patented.

*Male, or pollen, parent.*—Proprietary selection of *Gerbera hybrida* identified as code number FL 63, not patented.

Propagation:

*Type.*—By cuttings and by tissue culture.

*Time to initiate roots, by cuttings, summer and winter.*—About 3.5 weeks at temperatures about 20° C.

*Time to initiate roots, by tissue culture, summer and winter.*—About 2.5 to 3 weeks at temperatures about 20° C.

*Time to produce a rooted young plant, by cuttings, summer and winter.*—About 3.5 weeks at temperatures about 20° C. to 26° C.

*Time to produce a rooted young plant, by tissue culture, summer and winter.*—About five to six weeks at temperatures about 20° C. to 26° C.

*Root description.*—Fibrous.

Plant description:

*Appearance.*—Herbaceous perennials that are typically grown as container or garden plants; compact and uniformly mounding plant habit, broadly upright and roughly globular in shape; numerous leaves arranged in basal rosettes and outwardly arching; dense and bushy habit; inflorescences held above the foliar plane on erect and strong basal scapes; moderately vigorous growth habit.

*Plant height, soil level to top of foliar plane.*—About 25.5 cm.

*Plant height, soil level to top of inflorescences.*—About 52.2 cm.

*Plant width.*—About 63.5 cm.

Leaf description:

*Arrangement.*—Alternate, simple.

*Length.*—About 34 cm.

*Width.*—About 13.4 cm.

*Shape.*—Narrowly obovate; runcinate.

*Apex.*—Obtuse.

*Base.*—Acuminate.

*Margin.*—Coarsely and irregularly angulate; sinuses divergent; undulate.

*Texture, upper surface.*—Sparsely pubescent along main vein; slightly bullate.

*Texture, lower surface.*—Densely tomentose.

*Venation pattern.*—Pinnate.

*Color.*—Developing leaves, upper surface: Close to 143A. Developing leaves, lower surface: Close to 137C. Fully expanded leaves, upper surface: Between 139A and 147A; venation, close to 144A to 144B. Fully expanded leaves, lower surface: Close to 147B; venation, close to 144B.

*Petioles.*—Length: About 8.4 cm. Diameter: About 5 mm. Strength: Strong. Texture, upper and lower surfaces: Sparsely pubescent. Color, upper surface: Close to 144B; towards the base, tinged with close to 182B. Color, lower surface: Close to 144B; towards the base, tinged with close to 182C.

Inflorescence description:

*Appearance.*—Composite inflorescence form with oblanceolate-shaped ray florets; solitary inflorescences borne on upright and strong scapes above the foliar plane; ray and disc florets arranged acropetally on a capitulum.

*Fragrance.*—None detected.

*Flowering season.*—Plants begin flowering about 16 weeks after planting; under garden conditions in The Netherlands, plants flower from early spring to late summer; plants can be flowered year-round in the greenhouse.

*Inflorescence longevity.*—Depending on the temperature, inflorescences last about two to four weeks on the plant; inflorescences not persistent.

*Quantity of inflorescences.*—Freely flowering habit with about nine open and developing inflorescences per plant at one time.

*Inflorescence buds.*—Height: About 1.7 cm. Diameter: About 3.8 cm. Shape: Flattened globular. Color: Close to 137D; immature ray florets, close to N144C; immature disc florets, close to between N186C and 203A.

*Inflorescence size.*—Diameter: About 10 cm. Depth (height): About 3.5 cm. Diameter of disc: About 3.9 cm. Receptacle height: About 5 mm. Receptacle diameter: About 6 mm. Receptacle color: Close to 155B.

*Ray florets.*—Quantity and arrangement: About 200 per inflorescence; 80 arranged in outer three whorls and 120 arranged in the inner four whorls. Orientation: About 60° from vertical. Length, outer ray florets: About 4.5 cm. Length, inner ray florets: About 2.5 cm. Width, outer ray florets: About 1.1 cm. Width, inner ray florets: About 4 mm. Shape: Oblanceolate. Apex: Acute. Base: Cuneate. Margin: Entire. Texture, upper surface: Smooth, glabrous; velvety. Texture, lower surface: Smooth, glabrous; slightly velvety; slightly longitudinally ridged. Color, inner and outer ray florets: When opening, upper surface: Towards the apex, about 70% of the ray floret, close to 40A; towards the base, about 30% of the ray floret, close to 9A. When opening, lower surface: Close to 1A. Fully opened, upper surface: Towards the apex, about 60% of the ray floret, close to 33B; towards the base, about 40% of the ray floret, close to 9A; color does not fade with development. Fully opened, lower surface: Close to 8A; color does not fade with development.

*Disc florets.*—Quantity and arrangement: About 150 massed at center of receptacle. Length: About 1.7 cm. Width: About 3.5 mm. Shape: Tubular. Apex: Acute; upper 20%, free. Base: Lower 80%, fused. Margin: Entire. Texture, upper and lower surfaces: Smooth, glabrous. Color, prior to opening: Apex: Close to 35B. Mid-section: Close to 11C. Base: Close to 145C. Color, when opening: Apex: Close to 40A. Mid-section: Close to 9A. Base: Close to 145C. Color, fully opened: Apex: Close to 33B. Mid-section: Close to 9A. Base: Close to 145C.

*Pappus.*—Quantity of hairs per floret: About 50. Length: About 6 mm. Diameter: Less than 1 mm. Texture: Soft. Color: Close to N79A.

*Phyllaries.*—Quantity and arrangement: About 80 per inflorescence arranged in about three whorls. Length: About 1.5 cm. Width (at base): About 2 mm. Shape: Lanceolate. Apex: Narrowly acute. Base: Cuneate. Margin: Entire. Texture, upper surface: Smooth, glabrous. Texture, lower surface: Densely tomentose. Color, upper surface: Close to 143B. Color, lower surface: Close to 143A to 143B.

*Scapes.*—Length: About 42.4 cm. Diameter: Distally and proximally, about 6 mm; mid-section, about 7 mm. Angle: About 10° from vertical. Strength: Strong. Texture: Densely tomentose. Color: Close to 144A; distally, close to 147B; proximally, close to 180A to 180B.

*Reproductive organs.*—Androecium (present on disc florets only): Quantity per floret: Five. Filament length: About 7 mm. Filament color: Close to 11D. Anther shape: Lanceolate. Anther length: About 4 mm. Anther color: Close to 153D. Pollen amount: Scarce. Pollen color: Close to 15A. Gynoecium (present only on ray florets): Quantity per floret: One. Pistil length: About 1.2 cm. Stigma shape: Cleft. Stigma color: Close to 8A. Style length: About 1.15 cm. Style color: Close to 11C to 11D. Ovary color: Close to 145D.

*Seeds and fruits.*—Seed and fruit production has not been observed on plants of the new *Gerbera*.

Disease & pest resistance: Resistance to pathogens and pests common to *Gerbera* plants has not been observed on plants of the new *Gerbera* grown under commercial production conditions.

Garden performance: Plants of the new *Gerbera* have been observed to have good garden performance and to tolerate high temperatures about 35° C. and to be cold hardy to USDA Hardiness Zone 8.

It is claimed:

1. A new and distinct *Gerbera* plant named 'Flocanoes' as illustrated and described.

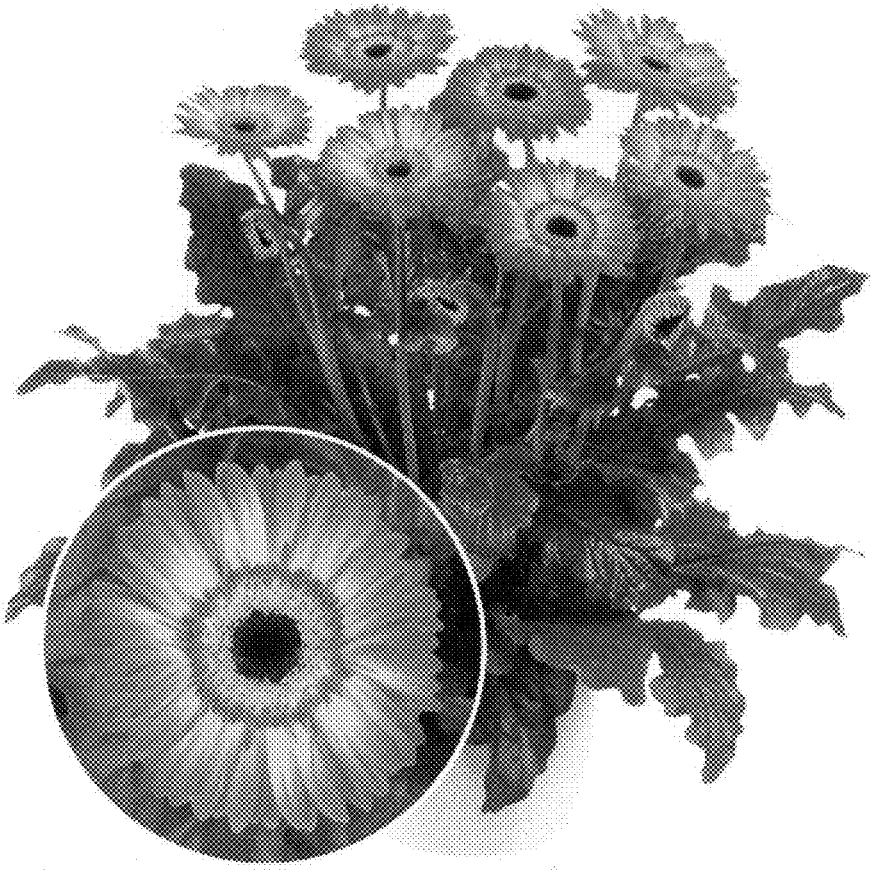

* * * * *